(12) United States Patent
Ostertag et al.

(10) Patent No.: US 10,131,634 B2
(45) Date of Patent: Nov. 20, 2018

(54) METHOD OF TREATING PAIN

(71) Applicant: Poseida Therapeutics, Inc., San Diego, CA (US)

(72) Inventors: Eric M. Ostertag, Lexington, KY (US); John Stuart Crawford, Lexington, KY (US)

(73) Assignee: Poseida Therapeutics, Inc., San Diego, CA (US)

( * ) Notice: Subject to any disclaimer, the term of this patent is extended or adjusted under 35 U.S.C. 154(b) by 0 days.

(21) Appl. No.: 14/303,711

(22) Filed: Jun. 13, 2014

(65) Prior Publication Data

US 2014/0329856 A1  Nov. 6, 2014

Related U.S. Application Data

(63) Continuation of application No. PCT/US2012/069753, filed on Dec. 14, 2012.

(60) Provisional application No. 61/576,619, filed on Dec. 16, 2011.

(51) Int. Cl.
| | | |
|---|---|---|
| *C07D 215/38* | (2006.01) | |
| *A61K 31/4709* | (2006.01) | |
| *A61K 31/00* | (2006.01) | |
| *A61K 45/06* | (2006.01) | |

(52) U.S. Cl.
CPC ............ *C07D 215/38* (2013.01); *A61K 31/00* (2013.01); *A61K 31/4709* (2013.01); *A61K 45/06* (2013.01)

(58) Field of Classification Search
CPC .. C07D 215/38; A61K 31/00; A61K 31/4709; A61K 45/06
See application file for complete search history.

(56) References Cited

U.S. PATENT DOCUMENTS

| | | | |
|---|---|---|---|
| 4,376,110 A | 3/1983 | David et al. | |
| 4,399,216 A | 8/1983 | Axel et al. | |
| 5,010,175 A | 4/1991 | Rutter et al. | |
| 5,288,514 A | 2/1994 | Ellman | |
| 5,506,107 A | 4/1996 | Cunningham et al. | |
| 5,506,337 A | 4/1996 | Summerton et al. | |
| 5,519,134 A | 5/1996 | Acevedo et al. | |
| 5,525,735 A | 6/1996 | Gallop et al. | |
| 5,539,083 A | 7/1996 | Cook et al. | |
| 5,549,974 A | 8/1996 | Holmes | |
| 5,569,588 A | 10/1996 | Ashby et al. | |
| 5,593,853 A | 1/1997 | Chen et al. | |
| 6,188,965 B1 | 2/2001 | Mayo et al. | |
| 6,403,312 B1 | 6/2002 | Dahiyat et al. | |
| 7,223,557 B2 | 5/2007 | Lee et al. | |
| 7,524,862 B2 | 4/2009 | Stenkamp et al. | |
| 7,998,993 B2 | 8/2011 | Perner et al. | |
| 8,084,616 B2 | 12/2011 | Gomtsyan et al. | |
| 9,376,450 B2 | 6/2016 | Allen et al. | |
| 2002/0072101 A1 | 6/2002 | Gaughan et al. | |
| 2004/0082779 A1 | 4/2004 | Voss et al. | |
| 2005/0267115 A1 | 12/2005 | Stenkamp et al. | |
| 2006/0194750 A1* | 8/2006 | Shuster ............... | C12N 15/1138 514/44 R |
| 2009/0131302 A1 | 5/2009 | Pasricha et al. | |
| 2009/0163545 A1* | 6/2009 | Goldfarb ....................... | 514/312 |
| 2009/0325975 A1 | 12/2009 | Buschmann | |
| 2010/0016293 A1 | 1/2010 | Smits et al. | |
| 2012/0148604 A1 | 6/2012 | Ostertag et al. | |

FOREIGN PATENT DOCUMENTS

| | | |
|---|---|---|
| EP | 0 135 781 | 4/1985 |
| WO | WO 1991/19735 | 12/1991 |
| WO | WO 1992/00091 | 1/1992 |
| WO | WO 1993/20242 | 10/1993 |
| WO | WO 1997/000271 | 1/1997 |
| WO | WO 2001/25277 A1 | 4/2001 |
| WO | WO 2002/44210 A2 | 6/2002 |
| WO | WO 2003/057843 | 7/2003 |
| WO | WO 2004/071413 | 8/2004 |
| WO | 2005/087742 * | 9/2005 |
| WO | WO 2005/089206 | 9/2005 |
| WO | 2005/103029 * | 11/2005 |
| WO | WO 2005/121100 | 12/2005 |
| WO | WO 2007/025613 A2 | 3/2007 |
| WO | WO 2008/003702 | 1/2008 |
| WO | WO 2008/015403 A1 | 2/2008 |
| WO | WO 2009/037707 A2 | 3/2009 |
| WO | WO 2009/055629 A2 | 4/2009 |
| WO | WO 2009/055749 A1 | 4/2009 |
| WO | WO 2009/061152 A2 | 5/2009 |
| WO | WO 2009/084034 A2 | 7/2009 |
| WO | WO 2011/022638 | 2/2011 |

(Continued)

OTHER PUBLICATIONS

Miller, J Bio Chem, vol. 286, No. 38, pp. 33469-33446, Sep. 2011.*
Morrison, Analytical Chemistry, vol. 81, No. 15, pp. 6186-6194, 2009.*
Kobayashi, Tetrahedron, vol. 60, pp. 11639-11645, 2004.*
Matrix Scientific, Material Safety Data Sheet, updatedSep. 25, 2010, pp. 1-3.*
Holzer, CA 154:153797, abstract only of Handbook of Experimental Pharmacology, 2009, vol. 194 (Sensory Nerves), p. 283-332.*
Knowles, Pain, vol. 141, 191-209, 2009.*
Aitman, T. J., et al, Progress and prospects in rat genetics: a community view, Nature Genetics, May 2008, pp. 516-522, vol. 40, No. 5.

(Continued)

*Primary Examiner* — D Margaret M Seaman
(74) *Attorney, Agent, or Firm* — Cooley LLP; Ivor R. Elrifi; Katherine J. Miller

(57) ABSTRACT

The instant application discloses methods of treating, reducing, or preventing pain in a mammal, which may include administering a compound capable of modulating a transient receptor potential channel. In one aspect, the TRP channel may be TRPC4. Types of pain contemplated by the present disclosure include acute, chronic, neuropathic, and nociceptive pain.

2 Claims, 9 Drawing Sheets

(56) References Cited

FOREIGN PATENT DOCUMENTS

WO    WO 2011/057843    5/2011

OTHER PUBLICATIONS

Ansel, H.C. et al., eds., *Pharmaceutical Dosage Forms and Drug Delivery Systems*, 7th Supp. Ed., Lippincott Williams & Wilkins Publishers, 1999.
Ausubel et al. (1987) Current Protocols in Molecular Biology, Greene Publishing and Wiley-Interscience, New York).
Bass, B.L., The Short Answer: One way of seeing what a gene does is to block its messenger RNA and note the effects. New work should make the approach more broadly applicable. Nature, vol. 411 (2001) pp. 428-429.
Bennett, G.J., et al., "A peripheral mononeuropathy in rat that produces disorders of pain sensation like those seen in man", Pain 33:87-107, (1988).
Berger and Kimmel, Preparation of cDNA and the Generation of cDNA Libraries: Overview, (1987) Methods in Enzymology, vol. 152: Guide to Molecular Cloning Techniques, San Diego: Academic Press, Inc.
Butler, M. et al, "Mammalian Cell Biotechnology: a Practical Approach", JRL Press (1991).
Campbell et al., Phosphonate Ester Synthesis Using a Modified Mitsunobu Condensation, J. Org. Chem., vol. 59 (1994) p. 658.
Cervero, M.D., F., et al., "Visceral Pain", The Lancet, vol. 353, Issue 9170, pp. 2145-2148, Jun. 19, 1999.
Chaplan, S.R., et al., "Quantitative assessment of tactile allodynia in the rat paw", J. Neurosci. Methods, 53(1):55-63, Jul. 1994.
Chen, et al., "Analogous" Organic Synthesis of Small-Compound Libraries: Validation of Combinatorial Chemistry in Small-Molecule Synthesis, J. Amer. Chem. Soc., vol. 116 (1994) p. 2661.
Chen, Y.-L., et al., "Nocistatin and nociceptin exert opposite effects on the excitability of central amygdale nucleus-periaquedactal gray projection neurons," Molecular and Cellular Neuroscience, 2009, pp. 76-88, vol. 40.
Cho et al., An Unnatural Biopolymer, Science, vol. 261 (Sep. 1993) p. 1303.
Clontech (Gossen, M. and Bujard, H.), Tight control of gene expression in mammalian cells by tetracycline-responsive promoters, Proc. Natl. Acad. Sci. USA 89: 5547-5551 (Jun. 1992).
Creighton, Proteins, W.HJ. Freeman and Company (1984).
D'Amour, et al., "A Method for Determining Loss of Pain Sensation", J. Pharmacol. Exp. Ther. 72:74-79 (1941).
Dubuisson, D., et al., "The formalin test: a quantitative study of the analgesic effects of morphine, meperidine, and brain stem stimulation in rats and cats", Pain, 4(2):161-74, Dec. 1977.
Elbashir, S.M. et al., Duplexes of 21-nucleotide RNAs mediate RNA interference in cultured mammalian cells, Nature, vol. 411 (May 2001) pp. 494-498.
Elg, S., et al., "Cellular Subtype Distribution and Developmental Regulation of TRPC Channel Members in the Mouse Dorsal Root Ganglion," The Journal of Comparative Neurology, 2007, pp. 35-46, vol. 503, Wiley-Liss, Inc.
Epps et al., Characterization of the steady-state and dynamic fluorescence properties of the potential-sensitive dye bis-(1,3-dibutylabarbituric acid) trimethine oxonol (Dibac4(3)) in model systems and cells, Chemistry and Physics of Lipids, vol. 69 (1994) pp. 137-150.
Freichel, M. et al., "Functional role of TRPC proteins in vivo: lessons from TRPC-deficient mouse models," Biochemical and Biophysical Research Communications, vol. 322 (2004) pp. 1352-1358.
Furka, General method for rapid synthesis of multicomponent peptide mixtures, Int. J. Peptide Protein Res., vol. 37 (1991) pp. 487-493.
Gennaro, A.R. ed., Remington: The Science and Practice of Pharmacy, 20th Ed., Lippincott, Williams & Wilkins, 2000.

Geurts, A.M., et al, Generation of gene-specific mutated rats using zinc-finger nucleases, Rat Genomics: Methods of Molecular Biology, 2010, pp. 211-225,vol. 597 (Abstract only).
Hagihara et al., Vinylogous Polypeptides: An Alternative Peptide Backbone, J. Am. Chem. Soc., vol. 114, No. 16 (1992) p. 6568-6570.
Hamill et al., Power Electronics: A Field Rich in Nonlinear Dynamics, Nature, vol. 294 (1981) pp. 462-464.
Hardman, J.G., et al., eds., Goodman & Gilman's The Pharmacological basis of Therapeutics, 10th Ed., McGraw-Hill Professional, New York, 2011.
Hargreaves, K., et al., "A new and sensitive method for measuring thermal nociception in cutaneous hyperalgesia", Pain, 32(1):77-88, Jan. 1988.
Hirschmann et al., Nonpeptidal Peptidomimetics with a B-D-Glucose Scaffolding. A Partial Somatostatin Agonist Bearing a Close Structural Relationship to a Potent, Selective Substance P Antagonist, J. Am. Chem.. Soc., vol. 114 (1992) pp. 9217-9218.
Hobbs Dewitt, et al., "Diversomers": An approach to nonpeptide, nonoligomeric chemical diversity, Proc. Natl. Acad. Sci. USA, vol. 90 (Aug. 1993) pp. 6909-6913.
Hosford, D.A. et al., A radiohistochemical measure of [3H]TCP binding to the activated NMDA-receptor-gated ion channel in rat brain, Brain Research, vol. 516 (1990) pp. 192-200.
Houghten et al., Generation and use of synthetic peptide combinatorial libraries for basic research and drug discovery, Nature, vol. 354 (Nov. 1991) pp. 84-86.
Hu, H.-Z., et al., "2-Aminoethoxydiphenyl Borate Is a common Activator of TRPV1, TRPV2, and TRPV3*," The Journal of Biological Chemistry, Aug. 20, 2004, pp. 35741-35748, vol. 279, No. 34, The American Society for Biochemistry and Molecular Biology, Inc.
Jacob, H.J., et al, Gene Targeting in the Rat: Advances and Opportunities, Trends Genet., Dec. 2010, pp. 510-518, vol. 26(12).
Jacob, H.J., et al, Rat genetics: attaching physiology and pharmacology to the genome, Nature Reviews|Genetics, Jan. 2002, pp. 33-42, vol. 3.
Jae-Pyo, J. et al, "The specific activation of TRPC4 by Gi protein subtype," Biochemical and Biophysical Research Communications, vol. 377(2) (Dec. 12, 2008) pp. 538-543.
Jayasena, S.D., Aptamers: An Emerging Class of Molecules That Rival Antibodies in Diagnostics, Clinical Chemistry, vol. 45, No. 9 (1999) pp. 1628-1650.
Johnson, D. et al, A fluorescent calmodulin that reports the binding of hydrophobic inhibitory ligands, *Biochem. J.* 211 (Jan. 1983), pp. 473-479.
Karabinos, A. et al, Essential roles for four cytoplasmic intermediate filament proteins in Caenorhabditis elegans development, Proc. Natl. Acad. Sci. USA, vol. 98, No. 14 (Jul. 2001) pp. 7863-7868.
Keown et al., Methods for Introducing DNA into Mammalian Cells, Methods in Enzymology, vol. 185 (1990) pp. 527-537.
Kim, S.H., et al., "An experimental model for peripheral neuropathy produced by segmental spinal nerve ligation in the rat", Pain 50:355-363, (1992).
Kirk, R.E., *Experimental Design, Procedures for Behavioral Sciences*, 3rd Ed., Wadsworth Publishing, 1994.
Kohler, G. et al., Continuous cultures of fused cells secreting antibody of predefined specificity, Nature, vol. 256 (Aug. 1975) pp. 495-497.
Liang et al., Parallel Synthesis and Screening of a Solid Phase Carbohydrate Library, Science, vol. 274 (Nov. 1996) pp. 1520-1522.
Lipkin, et al., MLH3: a DNA mismatch repair gene associated with mammalian microsatellite instability, Nature Genetics, vol. 25 (Jan. 2000) pp. 27-35.
Lu, B., Generation of rat mutants using a coat color-tagged Sleeping Beauty transposon system, Mamm Genome, 2007, pp. 338-346, vol. 18.
Mansour et al., Disruption of the proto-oncogene int-2 in mouse embryo-derived stem cells: a general strategy for targeting mutations to non-selectable genes, Nature, vol. 336 (Nov. 1988) pp. 348-352.

(56) References Cited

OTHER PUBLICATIONS

Mashimo, T, et al., Generation of knockout rats with X-linked severe combined immunodeficiency (X-SCID) using zinc-finger nucleases, PLoS One, Jan. 2010, pp. e8870 (1-7), vol. 5, Issue 1.
Misteli et al., Applications of the green fluorescent protein in cell biology and biotechnology, Nature Biotechnology, vol. 15 (Oct. 1997) pp. 961-964.
Neher, E. et al., The Patch Clamp Technique, Scientific American, vol. 266 (1992) pp. 44-51 [Abstract Only].
Otsuguro, K. et al., "Isoform-specific Inhibition of TRPC4 Channel by Phosphatidylinositol 4,5-Bisphosphate," The Journal of Biological Chemistry, vol. 283(15) (Apr. 11, 2008) pp. 10026-10036.
Plant, T.D. et al., "Receptor-operated cation channels formed by TRPC4 and TRPC5," Naunyn-Schmiedeberg's Archives of Pharmacology, vol. 371(4) (Apr. 1, 2005) pp. 266-276.
Randall et al., A Method for Measurement of Analgesic Activity on Inflamed Tissue, Arch. Int. Pharmacodyn, vol. 111, No. 4 (1957) pp. 409-419 [Title Only].
Rohacs, T., et al,. "Phospholipase C mediated modulation of TRPV1 Channels," Mol Neurobiol, 2008, pp. 153-163, vol. 37.
Rowe, R.C., et al., eds., Handbook of Pharmaceutical Excipients, 4th Ed., APhA Publications, 2003.
Sambrook et al. (1989), *Molecular Cloning: A Laboratory Manual*, 2nd Ed., vols. 1-3, Cold Spring Harbor Laboratory.
Schindl et al. The first ankyrin-like repeat is the minimum indispensable key structure for functional assembly of homo- and heteromeric TRPC4/TRPC5 channels, Cell Calcium 43 (2008) 260-269.
Schultz and Schimer, *Principles of Protein Structure*, Springer-Verlag (1979).
Stein, W.D., Transport and Diffusion Across Cell Membranes, Academic Press (1986).
Sung, T.S. et al., "Functional Characteristics of TRPC4 Channels Expressed in HEK 293 Cells," Molecules and Cells, vol. 27 (Feb. 28, 2009) pp. 167-173.
Tong, C., et al, Production of p53 gene knockout rats by homologous recombination in embryonic stem cells, Nature, Sep. 2010, pp. 211-213, vol. 467.
Ulloa, A. et al, "Reduction in TRPC4 expression specifically attenuates G-protein coupled receptor-stimulated increases in intracellular calcium in human myometrial cells," Cell Calcium, vol. 46 (1) (Jul. 1, 2009) pp. 73-84.
Vaughn et al., Human Antibodies with Sub-nanomolar Affinities Isolated from a Large Non-immunized Phage Display Library, Nature Biotechnology, vol. 14 (Mar. 1996) pp. 309-314.
Vinegar, R., et al., "Biphasic development of carrageenin edema in rats", J. Pharmacol. Exp. Ther., 168(1):96-103, Mar. 1969.
Watanabe, H., et al., "The Pathological Role of Transient Receptor Potential Channels in Heart Disease," Circulation Journal, Mar. 2009, pp. 419-427, vol. 73.
Wissenbach, U., et al., "TRP channels as potential drug targets," Science Direct, Biology of the Cell, Dec. 2003, pp. 47-54, vol. 96.
Wu, C.F. et al., Dissociated Neurons from Normal and Mutant *Drosophila* Larval Central Nervous System in Cell Culture, The Journal of Neuroscience., vol. 3, No. 9 (Sep. 1983) pp. 1888-1899.
Wu, D. et al., "TRPC4 in Rat Dorsal Root Ganglion Neurons is Increased after Nerve Injury and is Necessary for Neurite Outgrowth," The Journal of Biological Chemistry, vol. 283(1) (Jan. 4, 2008) pp. 416-426.
Xie, Q. et al., "Expression and functional evaluation of transient receptor potential channel 4 in bovine corneal endothelial cells," Experimental Eye Research, vol. 81(1) (2005) pp. 5-14.
Zamore, P.D., RNA interference: listening to the sound of silence, Natural Structural Biology, vol. 8, No. 9 (Sep. 2001) pp. 746-750.
Zaragoza, F., et al., "2-(4-Alkylpiperazin-1-yl) quinolines as a New Class of Imidazole-Free Histamine H3 Receptor Antagonists", Journal of Medicinal Chemistry, American Chemical Society, US, Jan. 13, 2005, vol. 47, No. 1, pp. 306-311.
Zochowski et al., Concepts in Imaging and Microscopy: Imaging Membrane Potential with Voltage-Sensitive Dyes, Biol. Bull, vol. 198 (Feb. 2000) pp. 1-21.
International Search Report and Written Opinion dated Feb. 10, 2011for Application No. PCT/US2010/046151.
International Search Report and Written Opinion dated Feb. 25, 2013 for Application No. PCT/US2012/069753.
U.S. Appl. No. 61/235,534, filed Aug. 20, 2009.
U.S. Appl. No. 61/247,612, filed Oct. 1, 2009.
U.S. Appl. No. 61/576,619, filed Dec. 16, 2011.
Alhaider, A.A., et al., "Enhancement of imipramine-induced rat brain beta-adrenoreceptor desensitization by subacute co-administration of trazodone, zimelidine, quipazine or 5-hydroxytryptophan," Psychophamacology, 1991, 103:351-356, 6 pgs.
European Exam Report dated Feb. 4, 2016 for Application No. EP 12 806 318.7, 6 pgs.
Hansen, B. W. et al. "Phosphoramides, XV. Phosphorus Pentoxide Amine Mixtures as Reagents in the Synthesis of 2-(Dialkylamino) quinolines", *Liebigs Annalen Der Chemie*, 1981, No. 8, pp. 1485-1491.
Pucilowski, O. et al. "Aggressive Behavior Inhibition by Serotonin and Quipazine Injected into the Amygdala in the Rat", *Behavioral and Neural Biology*, 1985, vol. 43, No. 1, pp. 58-68.
Saari, R. et al., "Microwave-assisted synthesis of quinoline, isoquinoline, quinoxaline and quinazoline derivatives as CB2 receptor agonists", *Bioorganic & Medicinal Chemistry*, 2011, vol. 19, No. 2, pp. 939-950.
Smith, J. A. et al. "Sequential and Selective Buchwald-Hartwig Amination Reactions for the Controlled Functionalization of 6-Bromo-2-chloroquinoline: Synthesis of Ligands for the Tec Src Homology 3 Domain", *Journal of Organic Chemistry*, 2008, vol. 73, No. 22, pp. 8880-8892.
Smits, R. A. et al. "Fragment based design of new H4 receptor-ligands with anti-inflammatory properties in vivo", *Journal of Medicinal Chemistry*, 2008, vol. 51, No. 8, pp. 2457-2467.
Swanson, D. M. et al. "Identification and Biological Evaluation of 4-(3-trifluoromethylpyridin-2-yl)piperazine-1-carboxylic Acid (5-trifluoromethylpyridin-2-yl)amide, a High Affinity TRPV1 (VR1) Vanilloid Receptor Antagonist", Journal of Medicinal Chemistry, 2005, vol. 48, No. 6, pp. 1857-1872.
Yamazaki, T. et al. "Synthesis in the Diazasteroid Group. V. (1). Synthesis of the 9,14-Diazasteroid System", *Journal of Heterocyclic Chemistry*, 1975, vol. 12, No. 5, pp. 973-979.
Yu, L. et al. "Discovery of Aminoglycoside Mimetics by NMR-Based Screening of *Escherichia coli* A-site RNA", *Journal of the American Chemical Society*, 2003, vol. 125, No. 15, pp. 4444-4450.
Zemlan, F.P. et al. "Noradrenergic and serotonergic mediation of spinal analgesia mechanisms", *European Journal of Pharmacology*, 1980, vol. 61, No. 2, pp. 111-124.
Michael Schaefer, et al., "Functional Differences between TRPC4 Splice Variants", J. Biological Chemistry, vol. 277(5), (2002), pp. 3753-3759.
Hussein N. Rubaiy, et al., Picomolar, Selective, and Subtype-specific Small-Molecule Inhibition of TRPC1/4/5 Channels, J. Biol. Chem. (2017) 292(20), pp. 8158-8173.
Melissa Miller, et al., "Identification of ML204, a Novel Potent Antagonist That Selectively Modulates Native TRPC4/C5 Ion Channels", J. Biol. Chem 286, (2011), pp. 33436-33446 (Supplemental data only, main article previously cited, pp. 1-12).
Westlund et al., "A Rat Knockout Model Impolicates TRPC4 in Visceral Pain Sensation", Neuroscience 262 (2014), pp. 165-175.
Zoltán Oláh, et al., "Anti-calmodulins and Tricyclic Adjuvants in Pain Therapy Block the TRPV1 Channel", (2007), PLoS One, vol. 6, Issue 6 e545, pp. 1-12.
L. Menendez, et al., "Calmodulin inhibitors induce spinal analgesia in rats", Brain Research 731 (1996), pp. 114-121.
Fu Jie, et al., "Canonical transient receptor potential 4 and its small molecule modulators", (2015), Sci China Life Science 58(1), pp. 39-47.
Kathleen R. Gogas, et al., "The Cold Bath Assay: A Simple and Reliable Method to Access Cold Allodynia in Neuropathic Rats", Analgesia, vol. 3, p. 111-118, 1997.

(56) References Cited

OTHER PUBLICATIONS

Manfred Gossen, et al., "Tight-Control of Gene Expression in Mammalian Cells by Tetracycline-responsive Promoters", Proc. Natl. Acad. Sci. USA, vol. 89, pp. 5547-5551, 1992.
Freirich et al., "Quantitative Comparison of Toxicityof AntiCancer Agents in Mouse, Rat, Hamster, Dog, Monkey, and Man", Cancer Chemotherarpy Reports 50(4), (1966), pp. 219-244.
Randall et al., "A method for measurement of analgesic activity on inflamed tissue", Arch. Int. Pharmacodyn. 111, pp. 409-419 (1957).
NCBI Reference Sequence: NC_005101.2 Rattus Norvegicus Strain BN/SsNHsdMCW chromosome 2, RGSC_v3.4, Apr. 5, 2010, p. 1-2.
NCBI Reference Sequence: NC_005120.2 "Rattus Norvegicus Strain BN/SsNHsdMCW chromosome X, RGSC v3.4" Apr. 5, 2010, p. 1-2.
Boesmans, W. et al. (2011) "TRP channels in neurogastroenterology: opportunities for therapeutic intervention" *Br J Pharmacol*, 162:18-37.

\* cited by examiner

METHOD OF TREATING PAIN

CROSS-REFERENCE TO RELATED APPLICATIONS

This application is a continuation of and claims priority to PCT Application No. PCT/US12/69753, filed Dec. 14, 2012, which claims priority to U.S. Provisional Application No. 61/576,619, filed Dec. 16, 2011, both of which are incorporated in their entirety by reference herein. This application also incorporates by reference U.S. Provisional Patent Application Ser. No. 61/235,534, filed Aug. 20, 2009, U.S. Provisional Patent Application Ser. No. 61/247,612, filed Oct. 1, 2009, and PCT/US10/46151, filed Aug. 20, 2010.

FIELD AND BACKGROUND OF INVENTION

Mammalian transient receptor potential (TRP) channels are described as six-transmembrane (6-TM) cation-permeable channels. TRP channels control the gating of voltage-dependent $Ca^{2+}$, $K^+$, and $Cl^-$, and are characterized as calcium-permeable channels with polymodal activation properties. TRP protein structure is thought to be a channel forming structure composed of six transmembrane (TM) domains with a pore domain (P) located between the fifth (S5) and sixth (S6) TMs. TRP channels are activated by three major mechanisms; receptor, ligand and environment direct activation. Receptor activation is carried out by G protein coupled receptors (GCPRs) and tyrosine kinases in three modes which result in liberation of $Ca^{2+}$ from intracellular stores: hydrolysis of phosphatidylinositol (4,5) bisphosphate (PIP2), diacylglycerol (DAG) and inositol (1,4,5) triphosphate (IP3). Ligand activation occurs by exogenous small molecules (capsaicin, icilin, 2-APB), endogenous lipids or metabolism products (diacylglycerols), purine nucleotides and metabolites (ADP-ribose), and inorganic ions. TRP channels are also activated by environmental triggers such as ambient temperature.

The TRPC subfamily was established by the identification of the first mammalian TRP, TRPC1. Common TRPC motifs are composed of 2-3 ankyrin-like domain repeats and a coiled-coil domain in the N-terminal, followed by six transmembrane domains, the C-term TRP box and a calmodulin (CaM) binding site. The CaM domain in TRPC4 is a calcium binding domain which resembles the CaM protein, which is normally small (~140+ amino acid in length) dumbbell-shaped composed of two structurally similar globular domains separated by a flexible hinge central helix. The globular domains are homologous and contain pairs of $Ca^{2+}$ binding helix-loop-helix motifs which are referred to as the EF hand motifs. The typical mechanism of calcium binding occurs at these EF hands, which are composed of two α-helices linked to a 12-residue loop. The EF hand domains become exposed to effectors and targets by protein conformational change. The exposed hydrophobic regions in turn bind basic amphiphilic helices (BAA helices). The hinge of CaM allows for the proteins harboring a CaM domain to contact and activate targets (FIG. 1). CaM is highly conserved in animals and plants and acts on many targets including ion channels.

TRPC5 is expressed homomerically and also heteromerically complexes with TRPC4. TRPC4 and TRPC5 are highly homologous, and are highly expressed in the human brain, uterus, ovary and kidney cells. TRPC4 is a nonselective cation channel which is uniquely activated by Gq/11 family GPCRs through activation of PLCβ, and receptor kinases and receptor tyrosine kinases. Although studies using TRPC4 have shown that activation requires phospholipase C (PLC) activity, neither IP3 nor DAG is sufficient to activate TRPC4. TRPC4 contains a PDZ-binding motif. PDZ domains are common structural motifs which aid proteins in signaling and anchoring transmembrane proteins to the cytoskeleton. PDZ domain scaffolding proteins, as well as signaling molecules, co-immunoprecipitate with TRPC4. PDZ domain is a common structural domain of 80-90 amino-acids found in the signaling proteins of bacteria, yeast, plants, viruses and animals. PDZ is an acronym combining the first letters of three proteins—post synaptic density protein (PSD95), Drosophila disc large tumor suppressor (DlgA), and zonula occludens-1 protein (zo-1)— which were first discovered to share the domain. PDZ domains are also referred to as DHR (Dlg homologous region) or GLGF (glycine-leucine-glycine-phenylalanine) domains. These domains help anchor transmembrane proteins to the cytoskeleton and hold together signaling complexes.

Almost every cell type scrutinized contains at least one TRP channel. This large family of physiological important channels has been implicated in many human diseases. Most of the TRP channels are conserved in mice, rats, and humans. Knockout mice studies have proven to be insightful for determining TRP channel functions. Trpc2 deficient mice are unable to distinguish male from female counterparts and TRPV6 is upregulated in prostate cancer. TRPC4 transcripts and protein are expressed in primary cultured mouse vascular endothelial cells (MAECs) and the channels can be activated by store-depleted protocols in MAECs. In Trpc4 deficient mice, agonist induced $Ca^{2+}$ entry is significantly reduced. Trpc4−/− mice exhibit significant decrease in endothelium-dependent vasorelaxation in the blood vessels. The Trpc4 deficient mice display decreased microvascular permeability, and have altered GABA transmitter release from thalamic interneurons. Although TRPC4 is expressed in the nervous system it has not been validated previously as a target for neuropathic pain and there were no known specific inhibitors for the channel.

The human TRPC4 protein contains multiple ankyrin domains throughout and within the N-terminus along with a coiled-coil domain. The N-terminus of TRPC4 is very important for subunit assembly and pore formation. Two regions in the N-terminus are essential for channel assembly in TRPC channels and more specifically TRCP4; the third and fourth ankyrin repeats and the region downstream the coiled-coil domain. The second and third ankyrin repeats are represented by F59-S137 in TRPC4. Both of these domains are able to self associate but have not been shown to interact with one another. The last 18 amino acids of the region downstream of the coiled-coil domain are represented in TRPC4 by 287-A RLKLAIKYRQKEFVAP-304, and in TRPC6 by 363-SRLKLAIK YEVKKFVAHP-380. These peptides have been identified to be involved in channel assembly of TRPCs and more specifically TRPC4. There are two domains in the TRPC4 protein that are responsible for oligomerization. The first domain contains the N-term ankyrin repeats and the coiled-coil domain (M1-P304) and the second domain corresponds to the putative pore region and the C-terminal tail (I516-L974). Two models exist in which the TRPC4 channel becomes functional upon subunit assembly. One model is that the third ankyrin repeat initiates a molecular zippering process. In this model each interacting domain would have the ability to tetramerize. In another model, the first interaction domain forms a dimer between two subunits and the second domain is responsible for the formation of a dimer between two other subunits. The N-terminal of both TRPC4 and TRPC5 including at least the first ankyrin repeat are essential for both homo and hetero-subunit assembly. TRPC4 protein homo and heteromeric pore formation is critical for protein function; therefore, agents that block TRPC4 multimeric formation are reasonable candidates for TRPC4 protein inhibitors.

Neuropathic pain is a chronic disease resulting from a dysfunction in the nervous system. This nervous system dysfunction often occurs due to peripheral nerve injury concentrated at the dorsal root ganglia (DRG), sensory neurons. Abnormal nervous function arises from injured axons, and from intact nociceptors that share receptivity with the injured nerve. The pathological conditions include prolonged hyperalgesia, allodynia, and loss of sensory function. The classical presentation of neuropathic pain includes ubiquitous pain not otherwise explainable, sensory defects, burning pain, pain to light on the skin and sudden pain attacks without a clear provocation. Inflammation and trauma are major causes of nerve injuries. The genetic disorders causing distorted connectivity, structure or survival of neurons may also result in neuropathic pain.

BRIEF SUMMARY OF THE INVENTION

Disclosed are methods of treating, reducing, or preventing pain in a mammal, comprising administering a compound as described herein. In one aspect, the compound may be capable of modulating a transient receptor potential channel, for example, TRPC4.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

FIG. 1 is a graph showing lower body licking in wild type rats after colon mustard infusion with Formula 1a.

FIG. 2 is a graph showing abdominal retractions in wild type rats after colon mustard infusion with Formula 1a.

FIG. 3 is a graph showing 50% mechanical threshold in wild type rats after colon mustard infusion with Formula 1a.

DETAILED DESCRIPTION OF THE INVENTION

Definitions

Figure 1:
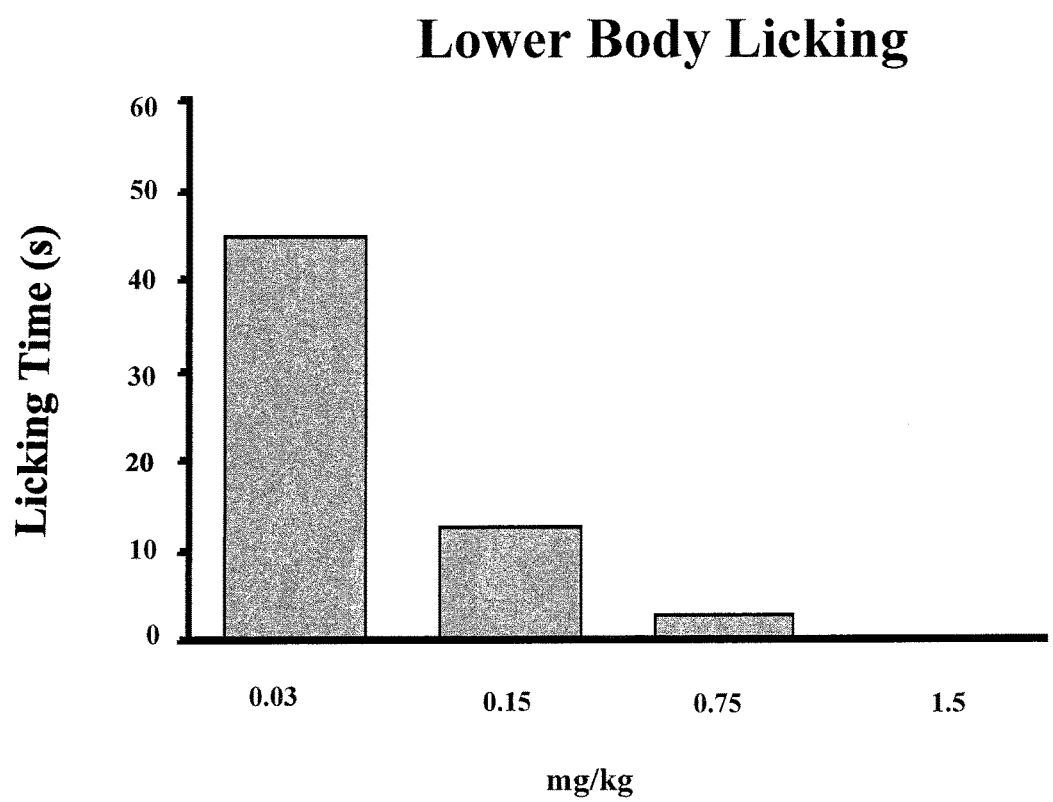

The present invention may be understood more readily by reference to the following detailed description of preferred embodiments of the invention and any Examples included therein and to any Figures and description thereof. Although any methods and materials similar or equivalent to those described herein can be used in the practice or testing of the present invention, the preferred methods, devices, and materials are now described. All references, publications, patents, patent applications, and commercial materials mentioned herein are incorporated herein by reference for the purpose of describing and disclosing the materials and/or methodologies which are reported in the publications which might be used in connection with the invention. Nothing herein is to be construed as an admission that the invention is not entitled to antedate such disclosure by virtue of prior invention.

Before the present compounds, compositions, articles, devices, and/or methods are disclosed and described, it is to be understood that this invention is not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

In this specification and in the claims which follow, reference will be made to a number of terms which shall be defined to have the following meanings:

As used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The term "alkyl" as used herein refers to a saturated straight or branched hydrocarbon, such as a straight or branched group of 1-22, 1-8, or 1-6 carbon atoms, referred to herein as (C1-C22)alkyl, (C1-C8)alkyl, and (C1-C6)alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "aryl" as used herein refers to a mono-, bi-, or other multi-carbocyclic, aromatic ring system. The aryl group can optionally be fused to one or more rings selected from aryls, cycloalkyls, and heterocyclyls. The aryl groups of this invention can be substituted with groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include, but are not limited to a monocyclic aromatic ring system, wherein the ring comprises 6 carbon atoms, referred to herein as "(C6)aryl."

"Alkyl," "alkenyl," "alkynyl," "alkoxy," "amino," and "amide" groups can be substituted with or interrupted by or branched with at least one group selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, thioketone, ureido, and nitrogen. The substituents may be branched to form a substituted or unsubstituted heterocycle or cycloalkyl.

"Agonists" are molecules or compounds that stimulate one or more of the biological properties of a receptor. These may include, but are not limited to, small organic and inorganic molecules, peptides, peptide mimetics and agonist antibodies. The term "antagonist" is used in the broadest sense and refers to any molecule or compound that blocks, inhibits or neutralizes, either partially or fully, a biological activity mediated by a receptor by preventing the binding of an agonist. Antagonists may include, but are not limited to, small organic and inorganic molecules, peptides, peptide mimetics and neutralizing antibodies.

As used herein, the terms "comprising," "containing," "having" and "including" are used in their open, non-limiting sense.

As used herein, an "effective amount" generally is the minimum dose necessary to achieve the desired effect of "treating, reducing, or preventing pain," as defined below.

"Enhance" as used herein, includes any increase in the functional activity of the ion channels.

"Optional" or "optionally" means that the subsequently described event or circumstance may or may not occur, and that the description includes instances where said event or circumstance occurs and instances where it does not.

"Pain" means a sensory experience perceived by nerve tissue distinct from sensations of touch, pressure, heat and cold. The range of pain sensations, as well as the variation of perception of pain by individuals, renders a precise definition of pain nearly impossible. In the context of the present invention, "pain" is used in the broadest possible sense and includes nociceptive pain, such as pain related to tissue damage and inflammation, pain related to noxious stimuli, acute pain, chronic pain, and neuropathic pain.

The level of stimulation at which pain becomes noted is referred to as the "pain threshold." Analgesics are pharmaceutical agents which relieve pain by raising the pain threshold without a loss of consciousness. After administration of an analgesic drug, a stimulus of greater intensity or longer duration is required before pain is experienced. In an individual suffering from hyperalgesia an analgesic drug may have an anti-hyperalgesic effect. In contrast to analgesics, agents such as local anaesthetics block transmission in peripheral nerve fibers thereby blocking awareness of pain. General anaesthetics, on the other hand, reduce the awareness of pain by producing a loss of consciousness.

"Acute pain" is often short-lived with a specific cause and purpose; generally produces no persistent psychological reactions. Acute pain can occur during soft tissue injury, and with infection and inflammation. It can be modulated and removed by treating its cause and through combined strategies using analgesics to treat the pain and antibiotics to treat the infection.

"Chronic pain" is distinctly different from and more complex than acute pain. Chronic pain has no time limit, often has no apparent cause and serves no apparent biological purpose. Chronic pain can trigger multiple psychological problems that confound both patient and health care provider, leading to feelings of helplessness and hopelessness. The most common causes of chronic pain include low-back pain, headache, recurrent facial pain, pain associated with cancer and arthritis pain.

Pain that is caused by damage to neural structures is often manifest as a neural supersensitivity or hyperalgesia and is termed "neuropathic" pain. Pain can also be "caused" by the stimulation of nociceptive receptors and transmitted over intact neural pathways, such pain is termed "nociceptive" pain. In one embodiment, the methods of the invention may be used to treat neuropathic pain. Neuropathic pain typically is long-lasting or chronic and can develop days or months following an initial acute tissue injury. Symptoms of neuropathic pain can involve persistent, spontaneous pain, as well as allodynia, which is a painful response to a stimulus that normally is not painful, hyperalgesia, an accentuated response to a painful stimulus that usually a mild discomfort, such as a pin prick, or hyperpathia, a short discomfort becomes a prolonged severe pain. Neuropathic pain generally is resistant to opioid therapy. Neuropathic pain can be distinguished from nociceptive pain or "normal pain," which is pain caused by the normal processing of stimuli resulting from acute tissue injury. In contrast to neuropathic pain, nociceptive pain usually is limited in duration to the period of tissue repair and usually can be alleviated by available opioid and non-opioid analgesics.

Visceral pain, as used herein, means pain that comes from the internal organs. Visceral pain has five important clinical characteristics: (1) it is not evoked from all viscera (organs such as liver, kidney, most solid viscera, and lung parenchyma are not sensitive to pain); (2) it is not always linked to visceral injury (cutting the intestine causes no pain and is an example of visceral injury with no attendant pain, whereas stretching the bladder is painful and is an example of pain with no injury); (3) it is diffuse and poorly localised; (4) it is referred to other locations; and (5) it is accompanied with motor and autonomic reflexes, such as the nausea, vomiting, and lower-back muscle tension that occurs in renal. *Lancet.* 1999 Jun. 19; 353(9170):2145-8.

"Modulating" as used herein includes any effect on the functional activity of the ion channels. This includes blocking or inhibiting the activity of the channel in the presence of, or in response to, an appropriate stimulator. Alternatively, modulators may enhance the activity of the channel.

The term "pharmaceutically acceptable composition" as used herein refers to a composition comprising at least one compound as disclosed herein formulated together with one or more pharmaceutically acceptable carriers.

As used herein, the term "pharmaceutically acceptable" refer to any molecular entity or composition that does not produce an adverse, allergic or other untoward or unwanted reaction when administered to a human or other mammal.

The term "pharmaceutically acceptable salt(s)" refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, matate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

As used herein, the term "subject" means any mammal or other vertebrate in which modulation of pain is desired, for example, a human, primate, horse, cow, dog, cat or bird.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring are designated as "cis" or "trans." The term "cis" represents substituents on the same side of the plane of the ring, and the term "trans" represents substituents on opposite sides of the plane of the ring. Mixtures of compounds wherein the substituents are disposed on both the same and opposite sides of plane of the ring are designated "cis/trans."

As used herein, a "suitable substituent" refers to a group that does not nullify the synthetic or pharmaceutical utility of the compounds of the invention or the intermediates useful for preparing them. Examples of suitable substituents include, but are not limited to: C1-22, C1-8, and C1-6 alkyl, alkenyl or alkynyl; C1-6 aryl, C2-5 heteroaryl; C3-7 cycloalkyl; C1-22, C1-8, and C1-6 alkoxy; C6 aryloxy; —CN; —OH; oxo; halo, carboxy; amino, such as —NH (C1-22, C1-8, or C1-6 alkyl), —N(C1-22, C1-8, and C1-6 alkyl)2, —NH((C6)aryl), or —N((C6)aryl)2; formyl; ketones, such as —CO(C1-22, C1-8, and C1-6 alkyl), —CO ((C6 aryl) esters, such as CO2(C1-22, C1-8, and C1-6 alkyl) and —CO2 (C6 aryl). One of skill in art can readily choose a suitable substituent based on the stability and pharmacological and synthetic activity of the compound of the invention.

By "treating, reducing, or preventing pain" is meant preventing, reducing, delaying onset of, or eliminating the sensation of pain in a subject before, during, or after it has occurred. As compared with an equivalent untreated control, such reduction or degree of prevention is at least 5%, 10%, 20%, 40%, 50%, 60%, 80%, 90%, 95%, or 100% as measured by any standard technique known in the art. To treat pain, according to the methods of this invention, the treatment does not necessarily provide therapy for the underlying pathology that is causing the painful sensation. Treatment of pain can be purely symptomatic.

While specific configurations and methods describing the present invention are discussed, it should be understood that this is done for illustrative purposes only. A person skilled in the pertinent art will recognize that other configurations and methods can be used without departing from the spirit and scope of the present invention. It will be apparent to a person skilled in the pertinent art that this invention can also be employed in a variety of other applications.

In one aspect, a method of treating, reducing, or preventing pain in a mammal is disclosed, wherein said method comprises the step of administering to a subject a therapeutically effective amount of a composition comprising a compound selected from Table 1 or Table 2, or a combination thereof, in combination with one or more pharmaceutically acceptable carriers.

In one aspect, the compound may comprise a substituted quinoline compound selected from Table 1. All compounds in Tables 1 and 2 may be prepared by the published methods of Miller et al., and an exemplary procedure is provided below (see supplementary material for J. Biol. Chemistry, Miller et al, vol. 286, pp. 33436-33446.)

Formula 1a is prepared as follows:

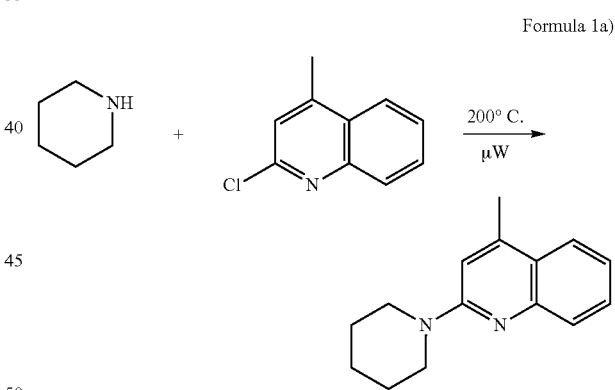

Formula 1a)

The chloroquinoline (100 mg, 0.56 mmol) and piperidine (0.22 ml, 2.25 mmol) were stirred in a microwave reaction vial. The vial was sealed and then irradiated under microwave at 200° C. with stirring for 15 min. LC/MS indicated reaction completion. The reaction mixture was diluted with MeOH and then concentrated under vacuum. The residue was dissolved in 3% aqueous HCl (10 ml) and washed with dichloromethane (2×5 ml). The aqueous layer was treated with 2 N NaOH until the pH was 8, resulting in a white slurry. The slurry was extracted with dichloromethane (3×20 ml). The combined organic layers were dried over $Na_2SO_4$ and concentrated to give 70 mg (55%) of the product as a white solid. $^1$H NMR (400 MHz, DMSO-$d_6$): δ 7.75 (d, J=8.1 Hz, 1H), 7.52-7.45 (m, 2H), 7.21-7.17 (m, 1H), 7.10 (s, 1H), 3.67 (bs, 4H), 2.54 (s, 3H), 1.62-1.55 (m, 6H). LC/MS: $R_T$=0.65 min, m/z=227.2 [M+H]$^+$.

TABLE 1

Substituted Quinoline Compounds (Formula I)

wherein R, R', and R" are as follows:

| R | R' | R" |
|---|---|---|
| piperidin-1-yl | H, CH₃, Et, or X (wherein X is a halogen) | H or alkyl |
| pyrrolidin-1-yl | H, CH₃, Et, or X | H or alkyl |
| azepan-1-yl | H, CH₃, Et, or X | H or alkyl |
| 4-methylpiperidin-1-yl | H, CH₃, Et, or X | H or alkyl |
| 3,4-dimethylpiperidin-1-yl | H, CH₃, Et, or X | H or alkyl |
| 4-methylpiperazin-1-yl | H, CH₃, Et, or X | H or alkyl |
| morpholin-4-yl | H, CH₃, Et, or X | H or alkyl |
| 4-hydroxypiperidin-1-yl | H, CH₃, Et, or X | H or alkyl |
| piperazin-1-yl | H, CH₃, Et, or X | H or alkyl |
| 4-(pyrimidin-2-yl)piperidin-1-yl | H, CH₃, Et, or X | H or alkyl |
| N,N-dimethylamino | H, CH₃, Et, or X | H or alkyl |
| N,N-diethylamino | H, CH₃, Et, or X | H or alkyl |
| 3,5-dimethylpiperidin-1-yl | H, CH₃, Et, or X | H or alkyl |

In one aspect, the compound may comprise a substituted piperidine compound described in Table 2.

TABLE 2

Substituted Piperidine Compounds

Formula II wherein R and R' are as follows:

| R | R' |
|---|---|
| Aryl, heteroaryl, alkyl, cycloalkyl, H | H, aryl, heteroaryl, alkyl, cycloalkyl |

In one aspect, the composition may comprise one or more compounds listed in Tables 1 and 2.

In one aspect, the compound may comprise a compound of Formula I, wherein R is

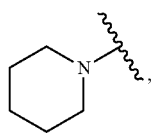 [SMILES: *N1CCCCC1]

R' is H, and R" is CH$_3$, and this compound is referred to as Formula 1a.

In one aspect, the composition is capable of modulating a Trcp4 receptor. Said modulation may be an antagonistic effect, or alternatively, an agonistic effect.

The effectiveness of a compound, for example a Trpc4 antagonist, in treating pain can be determined by observing one or more clinical symptoms or physiological indicators associated with pain, or via use of a pain model as described below.

The appropriate effective amount to be administered for a particular application of the methods can be determined by those skilled in the art, using the guidance provided herein. For example, an effective amount can be extrapolated from in vitro and in vivo assays as described herein above. One will recognize that the condition of the patient can be monitored throughout the course of therapy and that the effective amount of a Trpc4 antagonist that is administered can be adjusted accordingly.

One or more of the compounds disclosed herein may be administered in a pharmaceutical acceptable composition. The present disclosure also provides pharmaceutical compositions comprising compounds as disclosed herein, formulated together with one or more pharmaceutically acceptable carriers. These formulations include those suitable for oral, rectal, topical, buccal and parenteral (e.g. subcutaneous, intramuscular, intradermal, or intravenous) administration, although the most suitable form of administration in any given case will depend on the degree and severity of the condition being treated and on the nature of the particular compound being used.

Formulations suitable for oral administration may be presented in discrete units, such as capsules, cachets, lozenges, or tablets, each containing a predetermined amount of the compound as powder or granules; as a solution or a suspension in an aqueous or non-aqueous liquid; or as an oil-in-water or water-in-oil emulsion. As indicated, such formulations may be prepared by any suitable method of pharmacy which includes the step of bringing into association the active compound and the carrier or excipient (which may constitute one or more accessory ingredients). The carrier must be acceptable in the sense of being compatible with the other ingredients of the formulation and must not be deleterious to the recipient. The carrier may be a solid or a liquid, or both, and may be formulated with the compound as a unit-dose formulation, for example, a tablet, which may contain from about 0.05% to about 95% by weight of the active compound. Other pharmacologically active substances may also be present including other compounds. The formulations of the invention may be prepared by any of the well known techniques of pharmacy consisting essentially of admixing the components.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. In general, suitable formulations may be prepared by uniformly and intimately admixing the active compound with a liquid or finely divided solid carrier, or both, and then, if necessary, shaping the product. For example, a tablet may be prepared by compressing or molding a powder or granules of the compound, optionally with one or more accessory ingredients. Compressed tablets may be prepared by compressing, in a suitable machine, the compound in a free-flowing form, such as a powder or granules optionally mixed with a binder, lubricant, inert diluent and/or surface active/dispersing agent(s). Molded tablets may be made by molding, in a suitable machine, the powdered compound moistened with an inert liquid diluent.

Formulations suitable for buccal (sub-lingual) administration include lozenges comprising a compound in a flavored base, usually sucrose and acacia or tragacanth, and pastilles comprising the compound in an inert base such as gelatin and glycerin or sucrose and acacia.

Formulations of the present invention suitable for parenteral administration comprise sterile aqueous preparations of the compounds, which are approximately isotonic with the blood of the intended recipient. These preparations are administered intravenously, although administration may also be effected by means of subcutaneous, intramuscular, or intradermal injection. Such preparations may conveniently be prepared by admixing the compound with water and rendering the resulting solution sterile and isotonic with the blood. Injectable compositions according to the invention may contain from about 0.1 to about 5% w/w of the active compound.

Formulations suitable for rectal administration are presented as unit-dose suppositories. These may be prepared by admixing the compound with one or more conventional solid carriers, for example, cocoa butter, and then shaping the resulting mixture.

Formulations suitable for topical application to the skin may take the form of an ointment, cream, lotion, paste, gel, spray, aerosol, or oil. Carriers and excipients which may be used include Vaseline, lanoline, polyethylene glycols, alcohols, and combinations of two or more thereof. The active compound is generally present at a concentration of from about 0.1% to about 15% w/w of the composition, for example, from about 0.5% to about 2%.

The amount of active compound administered may be dependent on the subject being treated, the subject's weight, the manner of administration and the judgment of the prescribing physician. For example, a dosing schedule may involve the daily or semi-daily administration of the encapsulated compound at a perceived dosage of about 1 µg to about 1000 mg. In another embodiment, intermittent administration, such as on a monthly or yearly basis, of a dose of the encapsulated compound may be employed. Encapsulation facilitates access to the site of action and allows the administration of the active ingredients simultaneously, in theory producing a synergistic effect. In accordance with standard dosing regimens, physicians will readily determine optimum dosages and will be able to readily modify administration to achieve such dosages.

A therapeutically effective amount of a compound or composition disclosed herein can be measured by the therapeutic effectiveness of the compound. The dosages, however, may be varied depending upon the requirements of the patient, the severity of the condition being treated, and the compound being used. In one embodiment, the therapeutically effective amount of a disclosed compound is sufficient to establish a maximal plasma concentration. Preliminary doses as, for example, determined according to animal tests, and the scaling of dosages for human administration is performed according to art-accepted practices.

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices are preferable.

Data obtained from the cell culture assays or animal studies can be used in formulating a range of dosage for use in humans. Therapeutically effective dosages achieved in one animal model may be converted for use in another animal, including humans, using conversion factors known in the art (see, e.g., Freireich et al., Cancer Chemother. Reports 50(4):219-244 (1966) and Table 1 for Equivalent Surface Area Dosage Factors).

A pharmaceutical composition may be administered to a patient alone, or in combination with other supplementary active ingredients, agents, drugs or hormones. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilizate, tablet, pill, pellet, capsule, powder, syrup, elixir or any other dosage form suitable for administration.

The therapeutically effective dosage (i.e. ED50) may vary with the dosage form, route of administration, the subject's age, condition, and sex, as well as the severity of the medical condition in the subject. The dosage may be determined by a physician and adjusted, as necessary, to suit observed effects of the treatment.

The method may comprise administering an effective amount of a compound described herein together with one or more other agents including, but not limited to, one or more analgesic agents. In such "combination" therapy, it is understood that the antagonist can be delivered independently or simultaneously, in the same or different pharmaceutical compositions, and by the same or different routes of administration as the one or more other agents. In one aspect, a compound described herein may be administered in combination with a non-opioid analgesics, such as acetylsalicylic acid, choline magnesium trisalicylate, acetaminophen, ibuprofen, fenoprofen, diflusinal, and naproxen; or opioid analgesics, including morphine, hydromorphone, methadone, levorphanol, fentanyl, oxycodone, and oxymorphone. In addition to the above-listed treatments, neuropathic pain, which can be difficult to treat, has also been treated with anti-epileptics (e.g., gabapentin, carbamazepine, valproic acid, topiramate, phenyloin), NMDA antagonists (e.g., ketamine, dextromethorphan), topical lidocaine (for post-herpetic neuralgia), and tricyclic antidepressants (e.g., fluoxetine, sertraline and amitriptyline).

It is also envisioned that a pharmaceutical composition may optionally include a pharmaceutically acceptable carriers that facilitate processing of an active ingredient into pharmaceutically acceptable compositions. As used herein, the term "pharmacologically acceptable carrier" refers to any carrier that has substantially no long term or permanent detrimental effect when administered and encompasses terms such as "pharmacologically acceptable vehicle, stabilizer, diluent, auxiliary or excipient." Such a carrier generally is mixed with an active compound, or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., distilled, deionized water, saline; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in Pharmaceutical dosage forms and drug delivery systems (Ansel, H. C. et al., eds., Lippincott Williams & Wilkins Publishers, 7.sup.th ed. 1999); Remington: The Science and Practice of Pharmacy (Gennaro, A. R. ed., Lippincott, Williams & Wilkins, 20.sup.th ed. 2000); Goodman & Gilman's The Pharmacological Basis of Therapeutics (Hardman, J. G. et al., eds., McGraw-Hill Professional, $10^{th}$ ed. 2001); and Handbook of Pharmaceutical Excipients (Rowe, R. C. et al., APhA Publications, $4^{th}$ edition 2003).

A pharmaceutical composition may optionally include, without limitation, other pharmaceutically acceptable components, including, without limitation, buffers, preservatives, tonicity adjusters, salts, antioxidants, physiological substances, pharmacological substances, bulking agents, emulsifying agents, wetting agents, sweetening or flavoring agents, and the like. Various buffers and means for adjusting pH can be used to prepare a pharmaceutical composition disclosed in the present specification, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate and a stabilized oxy-chloro composition. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms.

Various routes of administration can be useful according to a method of the invention. Routes of peripheral administration useful in the methods of the invention encompass, without limitation, oral administration, topical administration, intravenous or other injection, and implanted minipumps or other extended release devices or formulations. A pharmaceutical composition useful in the invention can be peripherally administered, for example, orally in any acceptable form such as in a tablet, liquid, capsule, powder, or the like; by intravenous, intraperitoneal, intramuscular, subcutaneous or parenteral injection; by transdermal diffusion or electrophoresis; topically in any acceptable form such as in drops, creams, gels or ointments; and by minipump or other implanted extended release device or formulation.

Pain Models

The ability of a compound that treats pain may be confirmed using a variety of well-known assays as set forth herein.

Tail Flick Model: The tail-flick test (D'Amour et al., J. Pharmacol. Exp. and Ther. 72: 74-79 (1941)) is a model of acute pain. A gently-restrained rat is placed on a test stage such that a focused light source beams on the dorsal or ventral surface of the rat's tail. A photosensor is present on the test stage located opposite the light source. To begin the test, the rat's tail blocks the light, thus preventing the light reaching the photosensor. Latency measurement begins with the activation of the light source. When a rat moves or flicks its tail, the photosensor detects the light source and stops the measurement. The test measures the period of time (duration) that the rat's tail remains immobile (latent). Rats are tested prior to administration thereto of a compound of interest and then at various times after such administration.

Rat Tail Immersion Model: The rat tail immersion assay is also a model of acute pain. A rat is loosely held in hand while covered with a small folded thin cotton towel with its tail exposed. The tip of the tail is dipped into a, e.g., 52° C. water bath to a depth of two inches. The rat responds by either wiggling of the tail or withdrawal of the tail from the water; either response is scored as the behavioral end-point. Rats are tested for a tail response latency (TRL) score prior to administration thereto of a compound of interest and then retested for TRL at various times after such administration.

Carrageenan-induced Paw Hyperalgesia Model: The carrageenan paw hyperalgesia test is a model of inflammatory pain. A subcutaneous injection of carrageenan is made into the left hindpaws of rats. The rats are treated with a selected agent before, e.g., 30 minutes, the carrageenan injection or after, e.g., two hours after, the carrageenan injection. Paw pressure sensitivity for each animal is tested with an analgesymeter three hours after the carrageenan injection. See, Randall et al., Arch. Int. Pharmacodyn. 111: 409-419 (1957).

The effects of selected agents on carrageenan-induced paw edema can also be examined. This test (see, Vinegar et al., J. Phamacol. Exp. Ther. 166: 96-103 (1969) allows an assessment of the ability of a compound to reverse or prevent the formation of edema evoked by paw carrageenan injection. The paw edema test is carried out using a plethysmometer for paw measurements. After administration of a selected agent, a carrageenan solution is injected subcutaneously into the lateral foot pad on the plantar surface of the left hind paw. At three hours post-carrageenan treatment, the volume of the treated paw (left) and the untreated paw (right) is measured using a plethysmometer.

Formalin Behavioral Response Model: The formalin test is a model of acute, persistent pain. Response to formalin treatment is biphasic (Dubuisson et al., Pain 4: 161-174 (1977)). The Phase I response is indicative of a pure nociceptive response to the irritant. Phase 2, typically beginning 20 to 60 minutes following injection of formalin, is thought to reflect increased sensitization of the spinal cord.

Von Frey Filament Test (Chang model): The effect of compounds on mechanical allodynia can be determined by the von Frey filament test in rats with a tight ligation of the L-5 spinal nerve: a model of painful peripheral neuropathy. The surgical procedure is performed as described by Kim et al., Pain 50: 355-363 (1992). A calibrated series of von Frey filaments are used to assess mechanical allodynia (Chaplan et al., J. Neurosci. Methods 53: 55-63 (1994)). Filaments of increasing stiffness are applied perpendicular to the mid-plantar surface in the sciatic nerve distribution of the left hindpaw. The filaments are slowly depressed until bending occurred and are then held for 4-6 seconds. Flinching and licking of the paw and paw withdrawal on the ligated side are considered positive responses.

Chronic Constriction Injury: Heat and cold allodynia responses can be evaluated as described below in rats having a chronic constriction injury (CCI). A unilateral mononeuropathy is produced in rats using the chronic constriction injury model described in Bennett et al., Pain 33: 87-107 (1988). CCI is produced in anesthetized rats as follows. The lateral aspect of each rat's hind limb is shaved and scrubbed with Nolvasan. Using aseptic techniques, an incision is made on the lateral aspect of the hind limb at the mid-thigh level. The biceps femoris is bluntly dissected to expose the sciatic nerve. On the right hind limb of each rat, four loosely tied ligatures (for example, Chromic gut 4.0; Ethicon, Johnson and Johnson, Somerville, N.J.) are made around the sciatic nerve approximately 1-2 mm apart. On the left side of each rat, an identical dissection is performed except that the sciatic nerve is not ligated (sham). The muscle is closed with a continuous suture pattern with, e.g., 4-0 Vicryl (Johnson and Johnson, Somerville, N.J.) and the overlying skin is closed with wound clips. The rats are ear-tagged for identification purposes and returned to animal housing.

The Hargreaves Test: The Hargreaves test (Hargreaves et al., Pain 32: 77-88 (1998)) is also a radiant heat model for pain. CCI rats are tested for thermal hyperalgesia at least 10 days post-op. The test apparatus consists of an elevated heated (80-82.degree. F.) glass platform. Eight rats at a time, representing all testing groups, are confined individually in inverted plastic cages on the glass floor of the platform at least 15 minutes before testing. A radiant heat source placed underneath the glass is aimed at the plantar hind paw of each rat. The application of heat is continued until the paw is withdrawn (withdrawal latency) or the time elapsed is 20 seconds. This trial is also applied to the sham operated leg. Two to four trials are conducted on each paw, alternately, with at least 5 minutes interval between trials. The average of these values represents the withdrawal latency.

Cold Allodynia Model: The test apparatus and methods of behavioral testing is described in Gogas et al., Analgesia 3: 111-118 (1997). The apparatus for testing cold allodynia in neuropathic (CCI) rats consists of a Plexiglass chamber with a metal plate 6 cm from the bottom of the chamber. The chamber is filled with ice and water to a depth of 2.5 cm above the metal plate, with the temperature of the bath maintained at 0-4° C. throughout the test. Each rat is placed into the chamber individually, a timer started, and the animal's response latency was measured to the nearest tenth of a second. A "response" is defined as a rapid withdrawal of the right ligated hindpaw completely out of the water when the animal is stationary and not pivoting. An exaggerated limp while the animal is walking and turning is not scored as a response. The animals' baseline scores for withdrawal of the ligated leg from the water typically range from 7-13 seconds. The maximum immersion time is 20 seconds with a 20-minute interval between trials.

Using any of these assays and others known in the art, those skilled in the art recognize that $ED_{50}$ values and their standard errors of the mean can be determined using accepted numerical methods, see, e.g., Roger E. Kirk, Experimental Design: Procedures for the Behavioral Sciences, (Wadsworth Publishing, 3.sup.rd ed. 1994).

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Experimental Data:

The quinoline structure Formula 1a is tested in cells and rats. Wild type rats that are dosed with Formula 1a show dose responsive inhibition of pain (FIG. 1) with no obvious side effects, including no cardiotoxicity.

Figure 2:
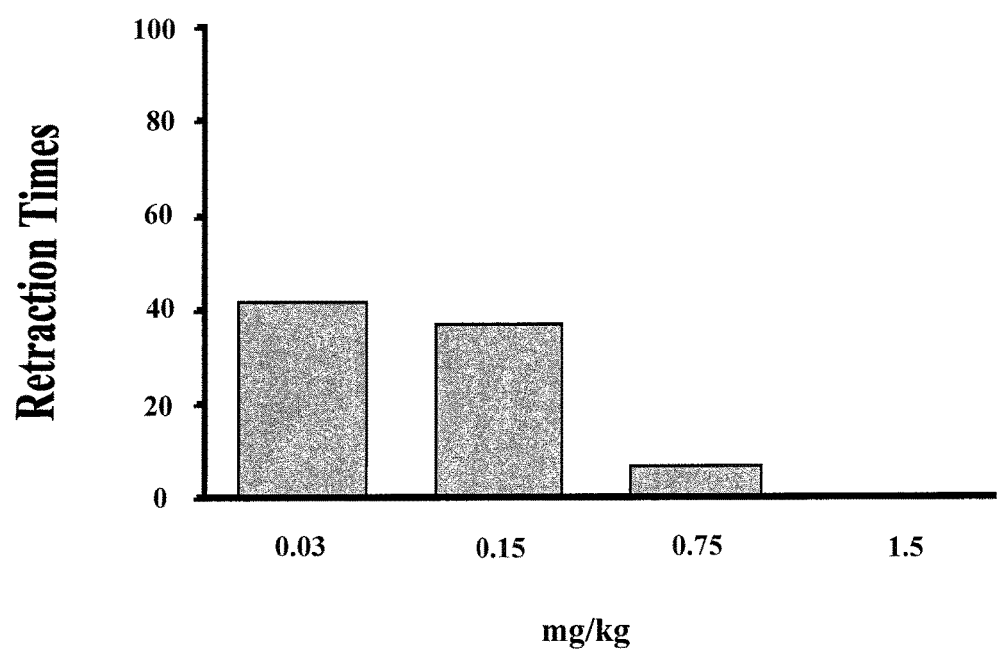
Figure 3:
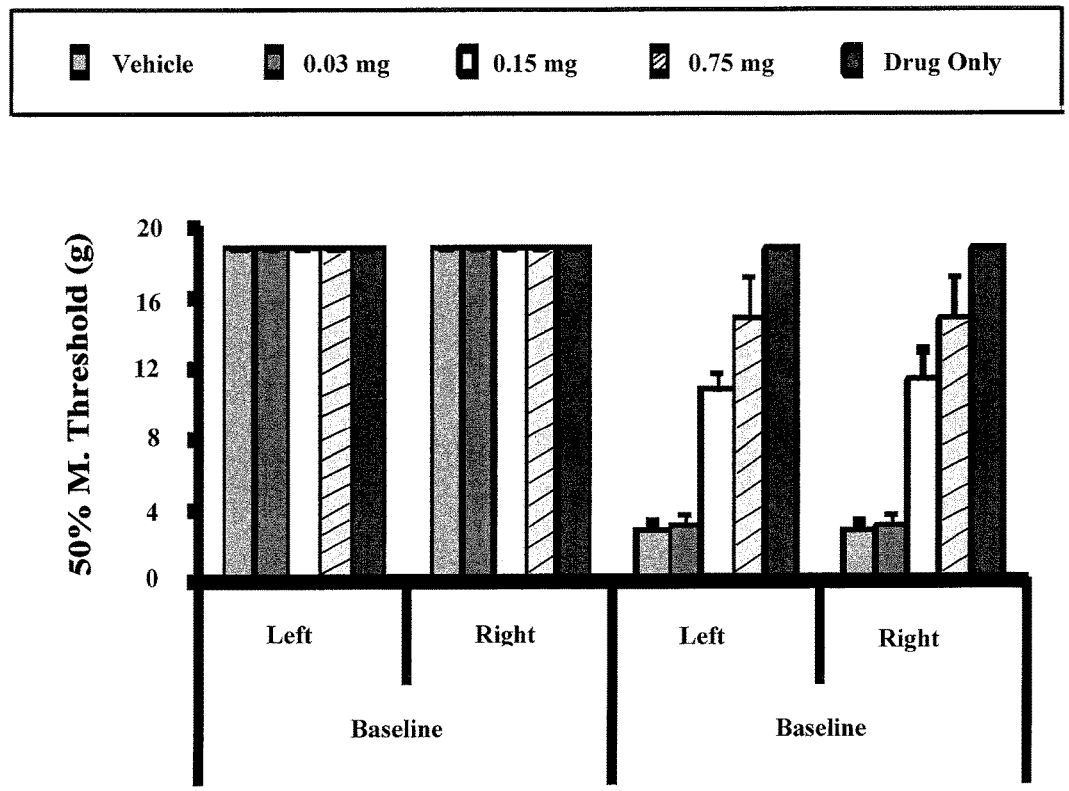

A. Spontaneous pain related behaviours and 50% mechanical threshold (on the paw) after colon mustard infusion (with Formula 1a) are shown in FIGS. 1-3.

Figure 4:
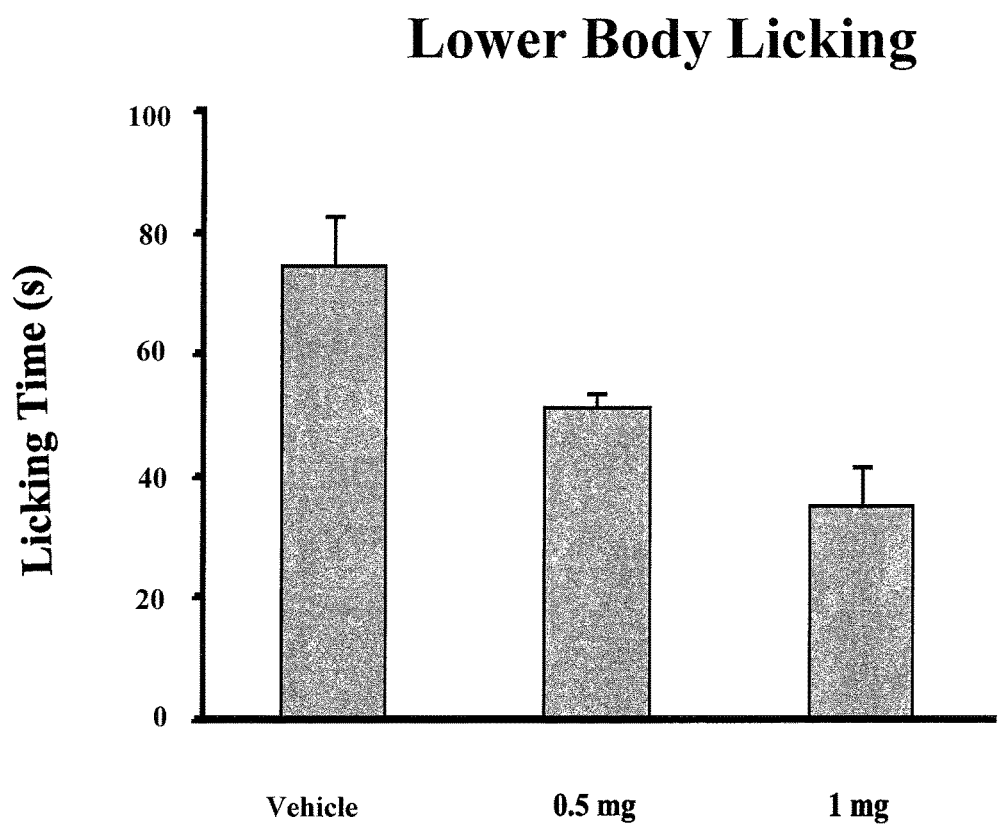
FIG. 4 a graph showing lower body licking in wild type rats after colon mustard infusion with ML204 oral feeding.
Figure 5:
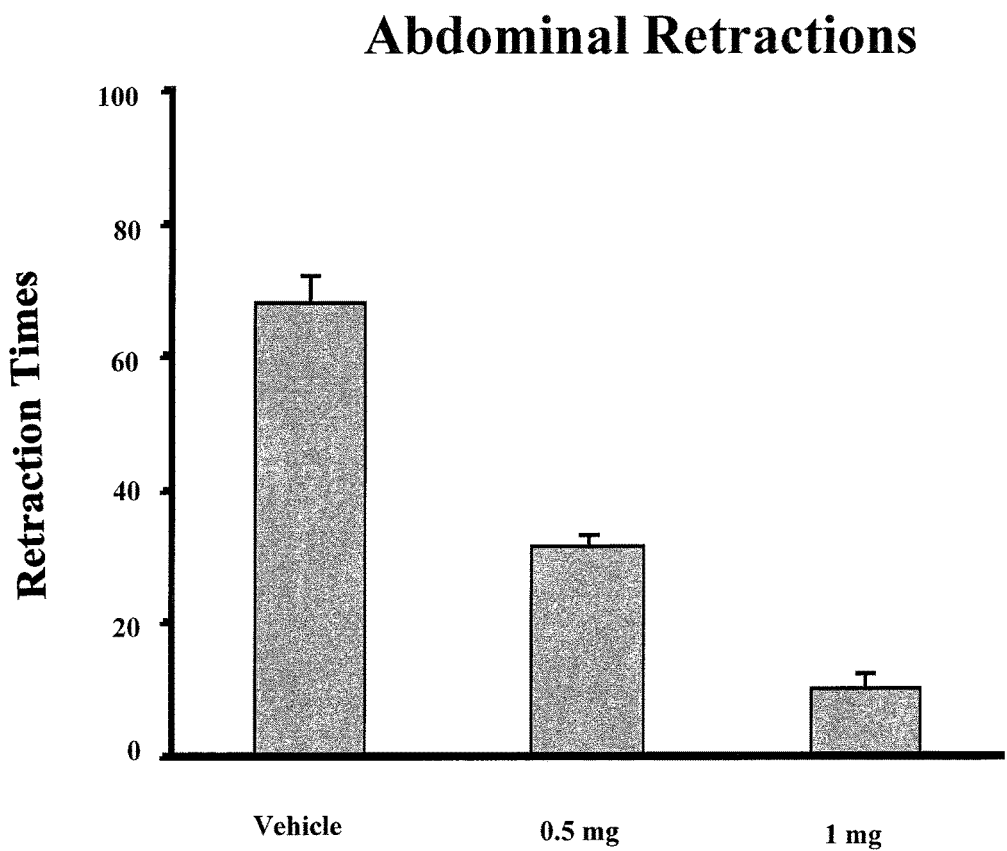
FIG. 5 is a graph showing abdominal retractions in wild type rats after colon mustard infusion with ML204 oral feeding.
Figure 6:
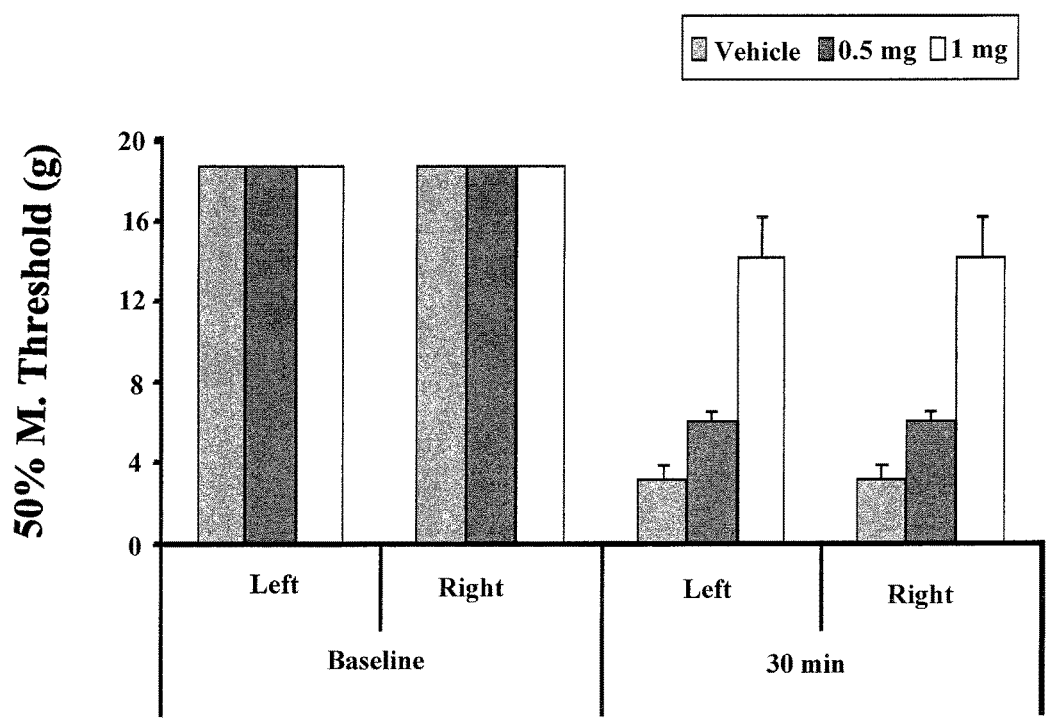
FIG. 6 is a graph showing 50% mechanical threshold in wild type rats after colon mustard infusion with ML204 oral feeding.

B. Spontaneous pain related behaviours and 50% mechanical threshold (on the paw) after colon mustard infusion (with ML204 oral feeding, n=4 for each group) are shown in FIGS. 4-6.

Figure 7:
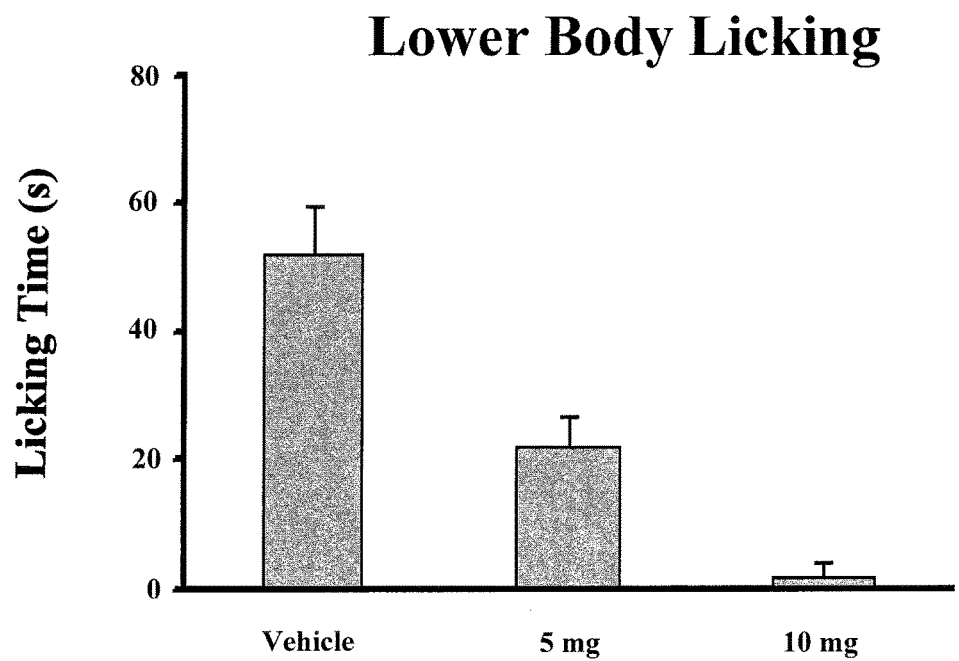
FIG. 7 is a graph showing lower body licking in wild type rats after colon mustard infusion with morphine pre-treatment.
Figure 8:
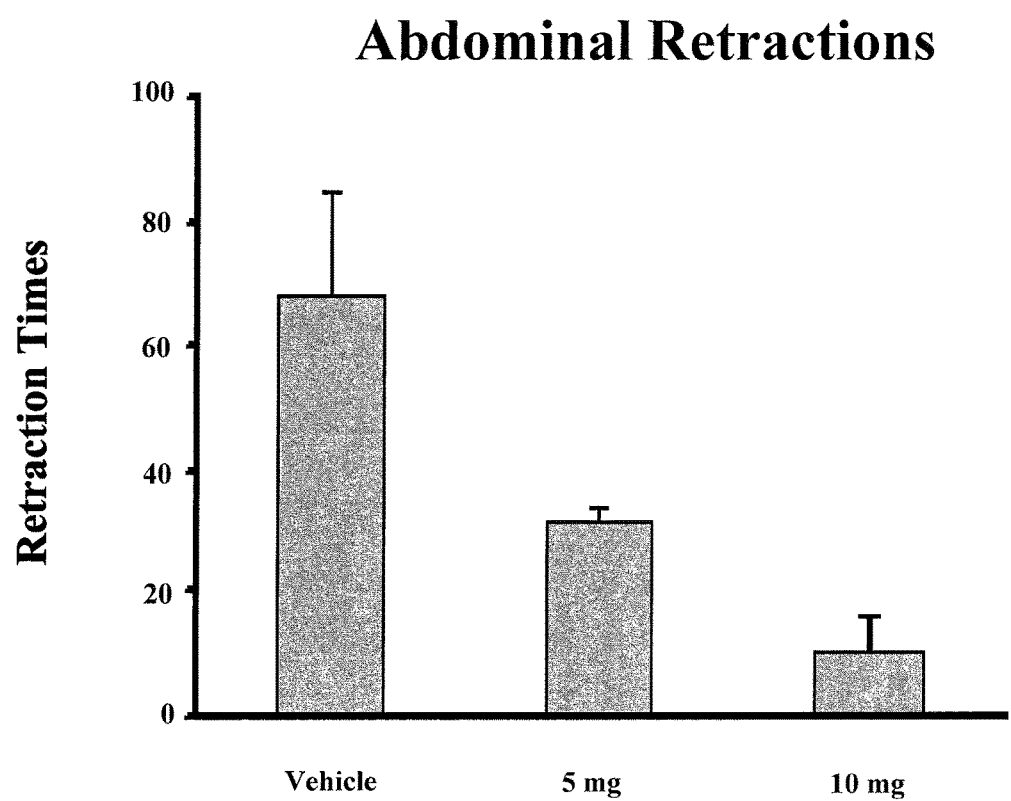
FIG. 8 is a graph showing abdominal retractions in wild type rats after colon mustard infusion with morphine pre-treatment.
Figure 9:
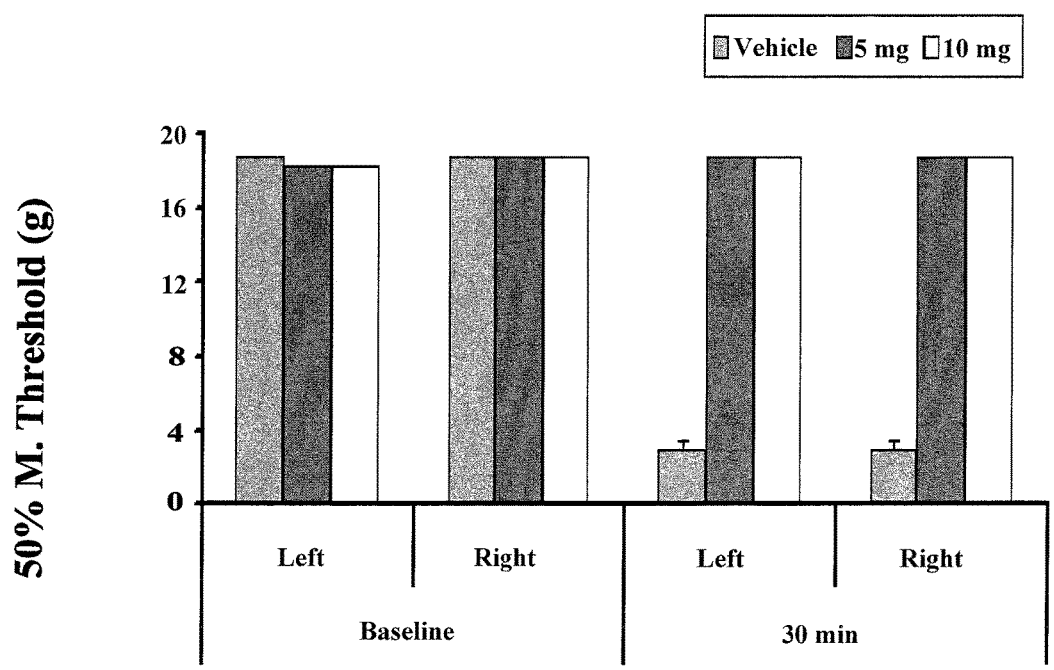
FIG. 9 is a graph showing 50% mechanical threshold in wild type rats after colon mustard infusion with morphine pre-treatment.

C. Morphine Equivalency. Pre-treatment with morphine requires much higher doses to inhibit pain related behaviors induced by intracolonic MO infusion. Spontaneous pain related behaviours and 50% mechanical threshold (on the paw) after colon mustard infusion (with morphine s.c., n=3 for each group) are shown in FIGS. 7-9.

The invention claimed is:

1. A method of treating, reducing, or preventing pain in a mammal, comprising administering a therapeutically effective amount of a composition to a human in need thereof, said composition comprising 4-methyl-2-piperidin-1-yl-quinoline having the formula

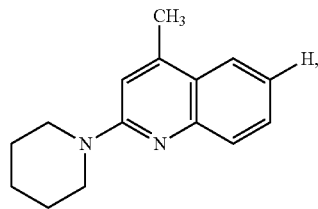

wherein said compound is administered orally, wherein the composition is capable of modulating Trpc4 activity to alleviate pain, wherein the pain is visceral.

2. The method of claim 1, wherein said composition further comprises one or more additional pharmaceutically active agents selected from non-opioid analgesics, opioid analgesics, anti-epileptics, NMDA antagonists, lidocaine, tricyclic antidepressants, and a combination thereof.

* * * * *